(12) United States Patent
McIntosh

(10) Patent No.: US 6,960,180 B2
(45) Date of Patent: Nov. 1, 2005

(54) VALVE OBTURATOR

(75) Inventor: Kevin D. McIntosh, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 701 days.

(21) Appl. No.: 10/122,798

(22) Filed: Apr. 15, 2002

(65) Prior Publication Data

US 2002/0110484 A1 Aug. 15, 2002

Related U.S. Application Data

(62) Division of application No. 09/187,781, filed on Nov. 6, 1998, now Pat. No. 6,409,967.

(51) Int. Cl.[7] .................. A61M 37/00; A61M 1/00; A61B 19/00; C02F 9/00; B01D 19/02
(52) U.S. Cl. ............. 604/6.15; 604/319; 604/403; 604/7; 96/179; 210/252
(58) Field of Search .............. 604/4.01, 6.01, 604/6.1, 6.15, 7, 6.13, 6.14, 19, 27, 65–67, 257, 262, 317–319, 321–323, 327, 403, 407, 408; 422/44–48, 1, 25, 26, 905; 125/DIG. 3, DIG. 24, 897, 912

(56) References Cited

U.S. PATENT DOCUMENTS

| 4,502,502 A | 3/1985 | Krug ................. 137/512.3 |
| 4,642,097 A | 2/1987 | Siposs .................. 604/119 |
| 4,722,725 A | 2/1988 | Sawyer et al. ............ 604/27 |
| 4,725,266 A | 2/1988 | Siposs .................. 604/119 |
| 4,758,224 A | 7/1988 | Siposs .................. 604/119 |
| 4,781,686 A | 11/1988 | Erickson ................ 604/118 |
| 4,932,612 A | 6/1990 | Blackwelder et al. ...... 244/207 |
| 4,979,883 A | 12/1990 | Neward ................. 417/441 |
| 5,158,539 A | 10/1992 | Koiff et al. ............. 604/31 |
| 5,411,705 A | 5/1995 | Thor et al. .............. 422/45 |
| 5,474,099 A | 12/1995 | Beohmer et al. .......... 137/35 |
| 5,707,356 A | 1/1998 | Paul .................... 604/119 |
| 5,791,372 A | 8/1998 | Mukumoto ............... 137/462 |

*Primary Examiner*—Patricia Bianco
(74) *Attorney, Agent, or Firm*—Tom Berry; Jeffrey J. Hohenshell

(57) ABSTRACT

An obturator prevents the tips or flaps of a duck-bill valve from self-adhering during storage or during sterilization procedures. The obturator holds the tips apart until the end-user is ready to use the valve. The duck-bill valve is used as an air outlet valve in blood reservoirs.

8 Claims, 3 Drawing Sheets

VALVE OBTURATOR

This application is a division of application Ser. No. 09/187,781, filed Nov. 6, 1998, now U.S. Pat. No. 6,409,967.

FIELD OF THE INVENTION

This invention relates to a blood reservoir for use in an extracorporeal blood circuit. In particular, this invention relates to a means for preventing self-adhesion of a one-way air outlet valve in the blood reservoir.

BACKGROUND OF THE INVENTION

In cardiopulmonary bypass operations, a patient's circulatory system is linked to a heart-lung machine to permit the extracorporeal circulation of blood. In these surgical procedures, a bypass circuit is created where venous blood bypasses the heart and is reintroduced into an artery. Also, cardiotomy blood is scavenged from the surgical site, combined with the venous blood, and reintroduced into the patient. The extracorporeal bypass circuit performs numerous functions, including removing emboli and particulate matter entrained in the blood, regulating the carbon dioxide and oxygen content of the blood, and regulating the blood temperature.

In the past, venous blood was filtered and collected in a venous reservoir and the cardiotomy blood was filtered and collected in a cardiotomy reservoir. Work in this art area has included efforts to simplify and improve these systems, as, for example, providing combined venous and cardiotomy reservoir systems. Other work has been directed to simplifying and improving the blood storage, filtration, and defoaming systems for both venous and cardiotomy blood.

In some systems, a sealed venous reservoir is used. This allows a vacuum to be pulled in the reservoir for the purpose of assisting the removal of blood from the patient. However, using such sealed systems creates a potential problem. During the surgical procedure, it is possible to develop either over-or under-pressure situations within the sealed reservoir. Either situation can lead to undesirable consequences for the patient. Therefore, it is known to use safety valves which can regulate the pressure within the sealed reservoir so that it does not exceed acceptable positive and negative pressure limits.

Safety valves include unidirectional valves such as umbrella valves and duck-bill valves. A unidirectional valve permits the escape of air when there is a positive or negative air pressure within the reservoir. Umbrella valves typically are used to vent negative pressure in a reservoir. Duck-bill valves typically are used to vent positive pressure. This valve includes two tips or flaps and an integral base defining a generally cylindrical opening. The tips or flaps butt against each other preventing the passage of air in or out of the reservoir, responding to positive pressure within the reservoir by spreading apart. Duck-bill valves in current use typically are comprised of silicone materials which are engineered to respond to certain pressures, thus allowing fluid to flow through the valve at desired pressures.

We have discovered that the tips or flaps of duck-bill valves used as air outlet valves in blood reservoirs can adhere together after long periods of time or after exposure to adverse environmental conditions. Typically such valves comprise silicone. This self-adhesion is an extremely undesirable situation, as a non-functioning valve can produce a build-up of pressure in a venous reservoir, resulting in reverse blood flow. Thus, a need exists to prevent the self-adhesion of duck-bill valve tips when the duck bill valve is used as a safety valve in blood reservoirs.

SUMMARY OF THE INVENTION

We have invented a device, termed an "obturator", which prevents the tips or flaps of a duck-bill valve from self-adhering during storage or during sterilization procedures. The obturator holds the tips apart until the end-user is ready to use the valve. The duckbill valve is used as an air outlet valve in blood reservoirs.

In one aspect, this invention is a method for preventing self-adhesion of the tips of a duck-bill valve during sterilization by providing an obturator having a plunger element; and inserting the plunger element between the tips of the duck-bill valve prior to sterilization.

The plunger element may be comprised of polymeric materials. Preferably, the plunger element is joined to a cap for ease of insertion and removal. More preferably, the plunger element and the cap are formed or molded from a single piece of plastic.

In a second aspect, this invention is a sealed blood reservoir comprising a top, a bottom, and a continuous sidewall, the top and bottom connected to the sidewall to form a sealed housing; the sealed housing defining an interior chamber; the housing having a blood inlet and a blood outlet in flow communication with the interior chamber; a duckbill valve having two tips and an integral body in communication with the interior chamber; and an obturator comprising a plunger element positioned between and separating the tips of the duck-bill valve.

In a third aspect, this invention is a method of preventing pressurization of a sealed blood reservoir by providing a sealed blood reservoir as described above, providing a duck-bill valve having two tips and an integral body in communication with the interior chamber of the reservoir; and inserting a plunger element between the tips of the duck-bill valve, wherein the plunger element prevents the tips of the duck-bill valve from self-adhering.

DETAILED DESCRIPTION OF THE INVENTION

The obturator of this invention is useful with duck-bill valves that are used in closed or sealed blood reservoir systems. A combined cardiotomy and venous blood reservoir is disclosed in U.S. Pat. No. 5,411,705 (Thor et al.), hereby incorporated herein by reference. This type of reservoir can be adapted and made into a sealed reservoir.

Figure 1:
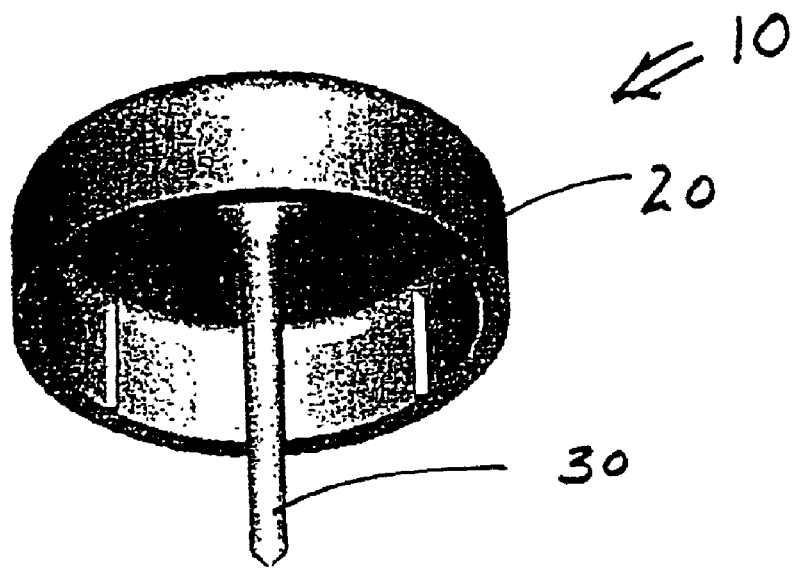
FIG. 1 is a perspective view of the obturator according to the present invention.
Figure 2:
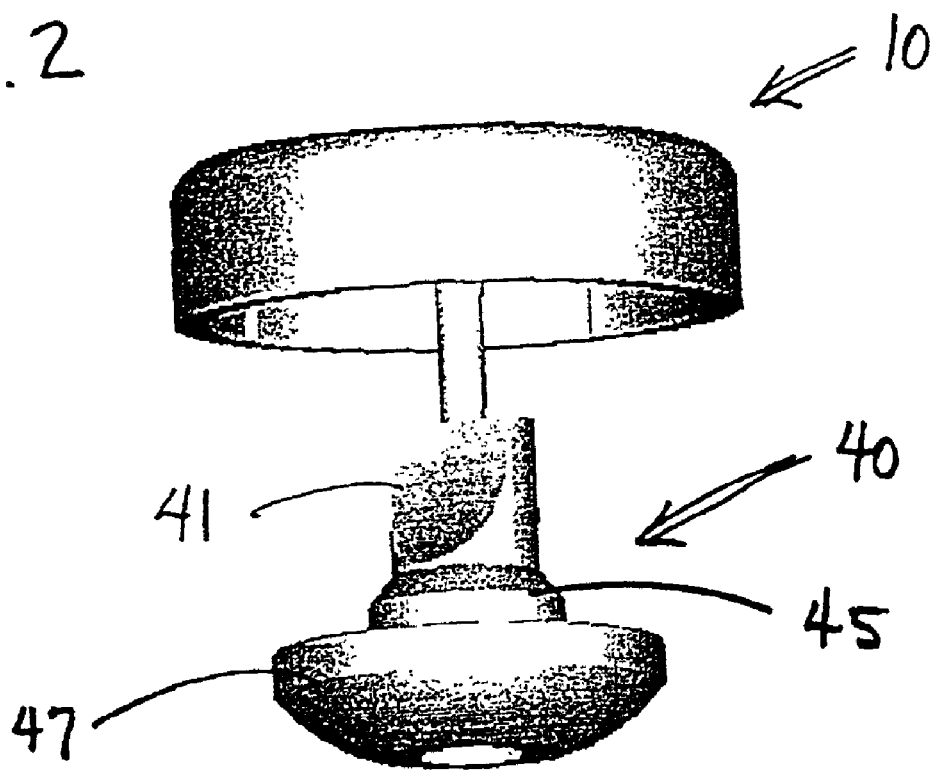
FIG. 2 is a perspective view of the obturator of this invention inserted between the tips of a duck bill valve.

The Figures illustrate the obturator and its placement in a representative duck-bill valve. The obturator was fabricated from polypropylene and placed in position in a duckbill valve made of silicone. FIG. 1 shows obturator 10 comprising cap 20 and plunger element 30. A perspective view of duck-bill valve 40 is with obturator 10 inserted is shown in FIG. 2.

Valve 40 comprises tips 41 and 43 integrally joined to body portion 45 which is itself joined to base 47. Base 47 may also function as an umbrella valve in response to negative pressure in the reservoir. The plunger element comprises a suitable material. A suitable material is one that is different from the valve material and one that will not chemically react with or adhere to the material of the valve during storage or sterilization procedures. Preferably, the obturator (i.e., the plunger element and the cap) is molded in a single piece from any suitable material. Such materials include, but are not limited to, polymeric materials comprising polyolefins, polytetrafluoroethylene (PTFE; also commercially available under the trade designation TEFLON™).

Figure 3:
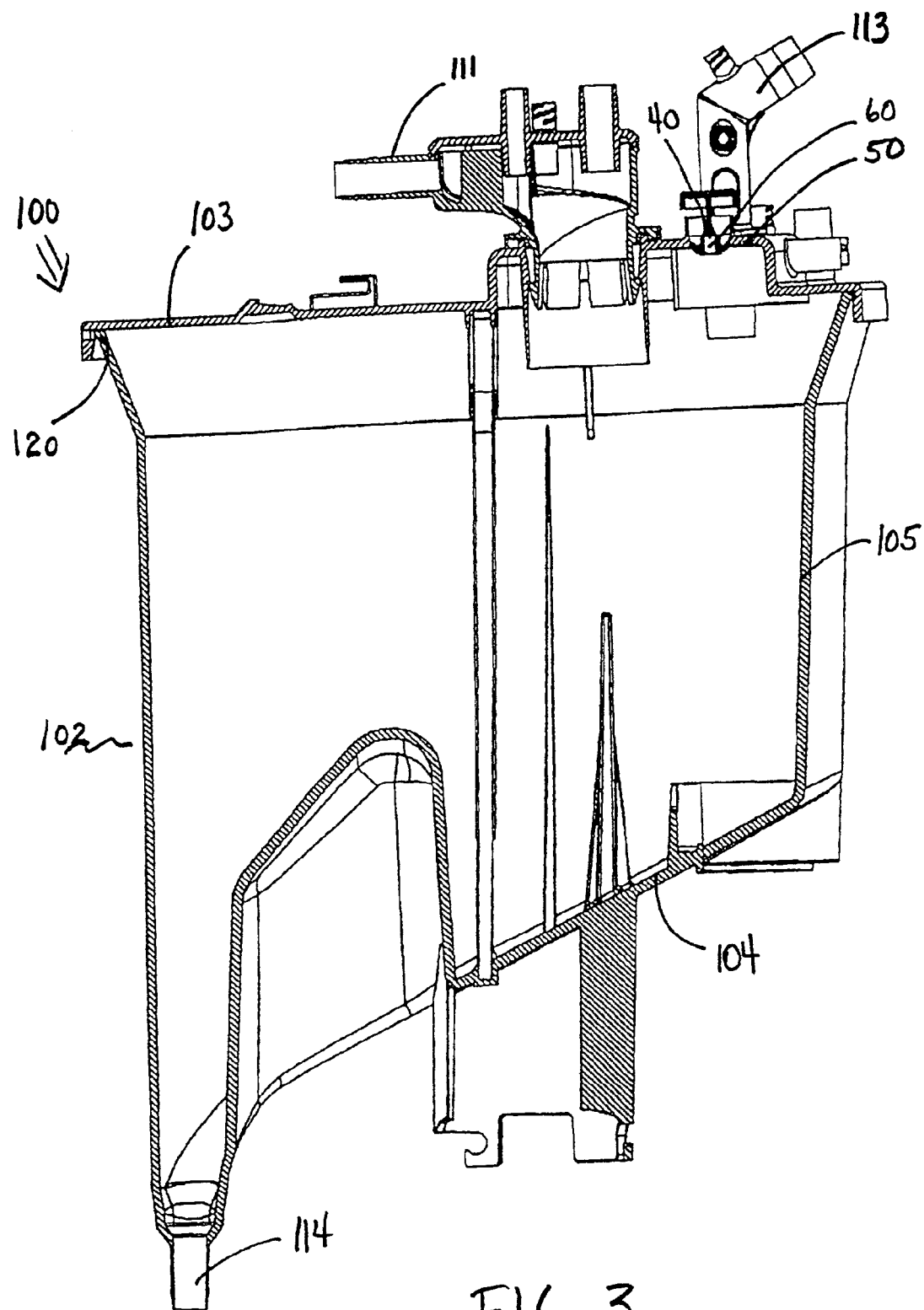
FIG. 3 is a cross-sectional view of a hard shell blood reservoir showing the placement of the duck-bill valve and the obturator of the present invention.

FIG. 3 shows a cross-sectional view of a combined venous and cardiotomy blood reservoir. This reservoir is sealed, that is, fluids such as blood or air do not leak into or out of the reservoir. Similar hard shell reservoirs are disclosed in U.S. Pat. No. 5,411,705 (Thor et al.). This reservoir comprises a rigid housing having a top, a bottom, and a continuous sidewall, where the top and bottom are connected to the sidewall to form an interior chamber. The interior chamber is in communication with a blood inlet and a blood outlet. A duck-bill valve is also in communication with the interior chamber.

The interior chamber typically includes a filter unit (not shown) that divides the reservoir into inlet and outlet chambers. These chambers are in fluid communication through the filter unit. A means for filtering and defoaming the blood is disposed within the inlet chamber. In the reservoir shown in FIG. 4, rigid housing 102 has a cover 103, a bottom 104, and a continuous sidewall 105 forming enclosed reservoir 100. Preferably, housing 102 is made of clear plastic so that medical personnel can observe the blood level in reservoir 100. Sidewall 105 and bottom 104 are integrally formed, molded plastic, and cover 103 is a separate plastic lid that fits onto top edge 120 and is sealed to it by means known in the art, such as by ultrasonic welding or by adhering the parts together with adhesive. Alternatively, cover 103 may be integrally molded with the sidewall by known methods. Blood flows into reservoir 100 through cardiotomy blood or venous blood inlets 111 and 113. The blood flows through filters to blood outlet 114. Plunger element 30 of obturator 10 is shown inserted between the tips of duck-bill valve 40 which is held in position within portion 50 of cover 103 of the reservoir.

Figure 4:
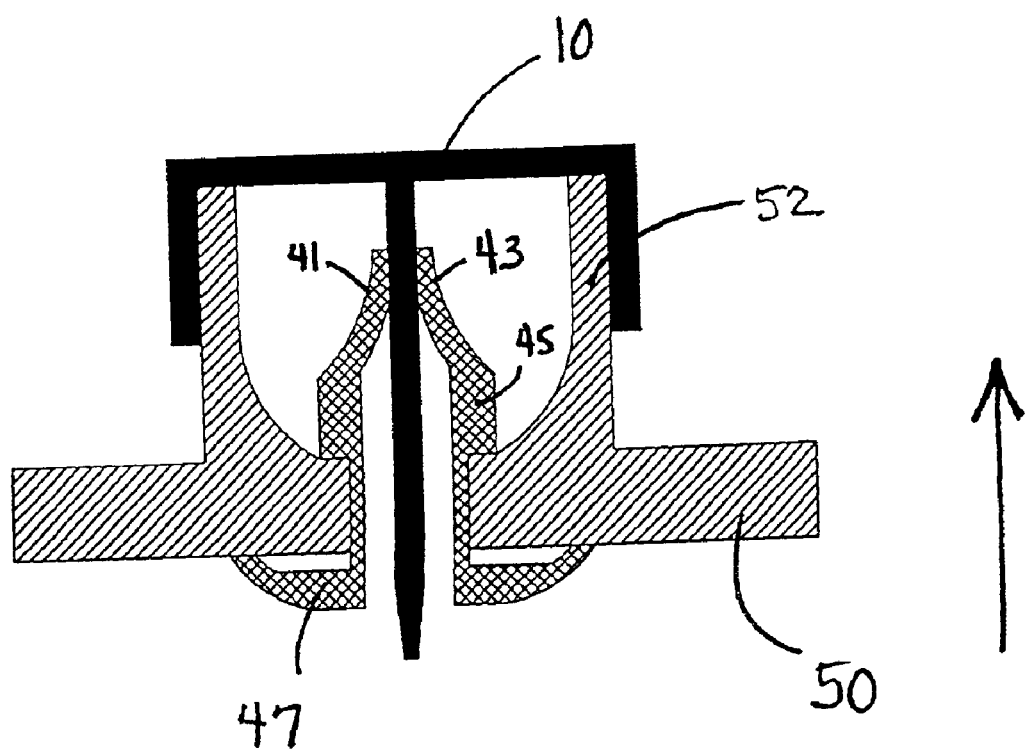
FIG. 4 is a cross-sectional view of the obturator and valve shown in FIG. 3.

FIGS. 3 and 4 show the valve and obturator positioned in the reservoir cover. The reservoir is a sealed system, and typically uses vacuum to assist the removal of blood from a patient. Outlet 60 is positioned at the top of the chamber and is in communication with the outlet chamber. Duck-bill valve 40 is held in position in outlet 60 by portion 50 of cover 103. Portion 50 is provided with annular projection 52. Base or umbrella valve 47 forms a seal with the underside of portion 50. Obturator 10 is inserted between the tips of valve 40. Cap 20 of obturator 10 fits over annular projection 52. If a positive pressure builds up in the reservoir, it is released through duck-bill valve 40. If a negative pressure occurs, this can be equalized by the admission of air through umbrella valve 47.

FIG. 4 shows a cross-sectional view of valve 40 installed on portion 50 of cover 103 of blood reservoir 100. The valve is in communication with the outlet chamber of the blood reservoir. The obturator is removed from the valve during cardiovascular surgery and permits the flow of air through the valve in the direction of the arrow if there is positive pressure within the reservoir and permits flow of air to the chamber by means of umbrella valve 47 in the event of negative pressure.

The utility of the obturator was tested by positioning the obturator plunger between the tips of a silicone duck-bill valve fitted in the housing of a blood reservoir, as illustrated in the Figures. This was sterilized under standard EtO (ethylene oxide) conditions. The obturator was removed. With positive air pressure in the reservoir, the valve tips separated, thereby preventing a positive pressure in the reservoir.

In contrast, a reservoir fitted with a silicone duck-bill valve was treated under the same sterilization conditions as above, but without the obturator. The tips of the valve adhered together after conventional sterilization, allowing pressure to build up within the interior chamber.

The obturator is useful when positioned during sterilization procedures and during long-term storage of reservoirs fitted with the valves. The obturator then is removed by the end-user of the blood reservoir before cardiovascular surgery.

Although particular embodiments of the invention have been disclosed herein in detail, this has been done for the purposes of illustration only, and is not intended to be limiting with respect to the scope of the appended claims. It is contemplated that various substitutions, alterations, and modifications may be made to the embodiments of the invention described herein without departing from the spirit and scope of the invention as defined by the claims.

What is claimed is:

1. A method of making a sealed blood reservoir including a duck-bill gas pressure relief valve having tips and for preventing self-adhesion of the tips of the duck-bill valve during sterilization, the method comprising:

making a sealed blood reservoir having the duck-bill valve;

providing an obturator having a plunger element;

inserting the plunger element between the tips of the duck-bill valve prior to sterilization;

sterilizing the sealed blood reservoir and duck-bill valve; and removing the plunger element of the obturator from the duck-bill valve before use of the sealed blood reservoir.

2. The method according to claim 1 further comprising providing a gas pressure differential across the duck-bill valve.

3. The method according to claim 2 wherein the sealed blood reservoir is a combined cardiotomy and venous blood reservoir, the step of providing a gas pressure differential across the duck-bill valve including pulling a vacuum in the reservoir.

4. The method of claim 1 wherein the step of providing an obturator further includes providing a cap.

5. A method of making a sealed combined cardiotomy and venous blood reservoir that includes a duck-bill gas pressure relief valve having tips and for preventing self-adhesion of the tips of the duck-bill valve during sterilization, the method comprising:

forming a duck-bill valve;

making a reservoir including mounting the duck-bill valve on the reservoir;

providing an obturator having a plunger element;

inserting the plunger element between the tips of the duck-bill valve before sterilization;

sterilizing the reservoir and duck-bill valve;

removing the plunger element of the obturator from the duck-bill valve before use of the reservoir; and providing a gas pressure differential across the duck-bill valve.

6. The method according to claim 5 wherein the step of providing a gas pressure differential across the duck-bill valve includes pulling a vacuum in the reservoir.

7. The method of claim 6 wherein the step of providing an obturator further includes providing a cap.

8. The method according to claim 5 wherein the step of forming the duck-bill valve comprises forming the duck-bill valve of silicone material.

\* \* \* \* \*